Figure 1:
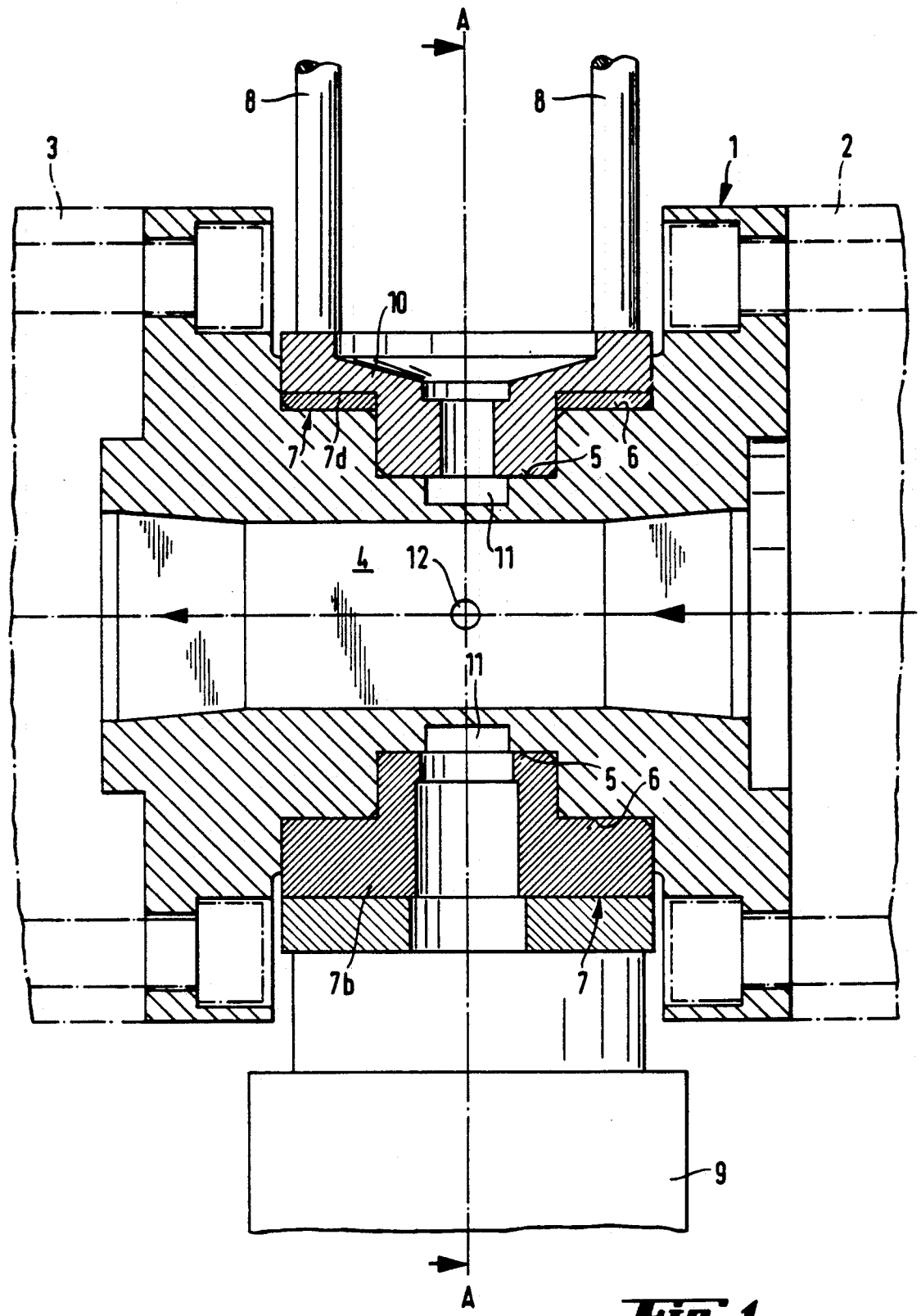

United States Patent [19]

Fritz et al.

[11] Patent Number: 5,005,194
[45] Date of Patent: Apr. 2, 1991

[54] METHOD AND APPARATUS FOR DETECTING IN CONFORMITY WITH PROCESS TIME MIXING RATIOS IN PLASTICS AND RUBBER COMPOUNDING

[75] Inventors: Hans-Gerhard Fritz, Uhingen; Rudi Löffel, Karlsruhe, both of Fed. Rep. of Germany

[73] Assignee: Hoechst Aktiengesellschaft, Fed. Rep. of Germany

[21] Appl. No.: 485,430

[22] Filed: Feb. 27, 1990

[30] Foreign Application Priority Data

Feb. 28, 1989 [DE] Fed. Rep. of Germany ....... 3906203

[51] Int. Cl.⁵ .............................................. G01N 23/06
[52] U.S. Cl. ......................................... 378/53; 378/55
[58] Field of Search .................................... 378/53, 55

[56] References Cited

U.S. PATENT DOCUMENTS 3,602,711 8/1971 Arora ................................... 378/53
4,429,410 1/1984 Jury et al. ............................. 378/53

Primary Examiner—Craig E. Church
Attorney, Agent, or Firm—Connolly & Hutz

[57] ABSTRACT

A method and an apparatus have been found, with the aid of which important properties can be determined during the extrusion of polymer melts:
continuous measurement of the density of pure polymers (density constancy)
plotting of p, v, T diagrams of plastics determination of percentagesf by volume and weight in polymer/filler or polymer/reinforcing agent mixtures
determination of proportions by weight of pigment in masterbatch preparation
determination of measuring data for statements going further regarding mixing and thermal homogeneity of the material.

Furthermore, the apparatus as a sensor is suitable as basic module for a closed control loop for monitoring and keeping constant porportions of filler.

2 Claims, 2 Drawing Sheets

METHOD AND APPARATUS FOR DETECTING IN CONFORMITY WITH PROCESS TIME MIXING RATIOS IN PLASTICS AND RUBBER COMPOUNDING

The invention relates to a method and an apparatus for detecting and quantifying in conformity with process time polymer/polymer, polymer/filler, polymer/reinforcing material, polymer/pigment, polymer/ceramic and polymer/metal powder mixing ratios in material compounding processes by means of an in-line measuring technique.

In the processing of plastics and elastomers, very differently composed polymer/additive mixtures are being employed to an increasing extent. The following may be mentioned by way of example: thermoplastics to which mineral fillers (talc, chalk, siliceous earth) have been added, polymers modified with fibrous reinforcing materials (glass fibers, carbon fibers), polymeric matrix materials (so-called masterbatches) to which dyestuffs and pigments ($Cr_2O_3$, $TiO_2$, $Fe_2O_3$) have been added, and last but not least so-called polyblends, which are produced by mixing two or three grades of thermoplastic or elastomer. The preparation of such mixtures is generally performed on single or twin screw extruders, the screws of which include numerous mixing and shearing sections specific to the task at hand. The feeding of the mixture components into the compounding unit is realized by means of volumetrically or gravimetrically operating metering systems. The mixture compounded in the extruder is transformed using a pelletizing station, coupled directly to the extruder, into cylindrical, lenticular, cuboid or spherical pellets, which are then molded in processing plants, such as for example injection-molding machines, blowmolding plants or extrusion lines, into finished products or semi-finished products. To an increasing extent, such compounding and molding steps are also being combined into single-stage processes.

The output rates in such mixture compounding processes are very high at 500 kg/h to 25,000 kg/h. Since variations over time in the mixture composition inevitably have significant retroactive effects on the properties of the end products produced, the mixture compounder endeavors to gain information continuously on the instantaneous percentage composition of the material mixture being produced at that particular time. Due to producer liability, he will also take trouble over the documentation of such information.

It is in keeping with the current state of the art to take samples from the stream of pellets at certain time intervals and to investigate them off-line, ie away from the process in a test laboratory, for their composition in terms of percentages by weight. In these investigations, a density gradient tube is used to determine the mixture density, from which the proportions by weight of the individual components can be calculated, provided that the material densities of the components of the mixture are known. In the case of minerally filled or reinforced polymers, such as with pigment concentrates which contain inorganic pigments, the mixture composition in terms of proportions by weight can also be determined by ashing of the samples. Another possibility of analyzing the composition of such mixtures is the use of Fourier transform infrared spectroscopy (FTIR). However, this method of analysis necessitates a laborious sample preparation and requires a very high expenditure on equipment. All the methods mentioned of determining the composition in terms of percentages by weight of such polymer/additive mixtures have in common that they are carried out off-line, as a result of which long nonproductive times occur, during which in some circumstances material of an unconforming grade is compounded. Apart from the fact that some of these methods are prone to disturbances (for example air adhering to the samples in density measurements by means of density gradient tube), they also do not provide analysis results which can form a basis for the development of closed process control loops.

To determine the composition of the mixtures in terms of proportions by weight in a way which conforms as far as possible to process time, a process rheometer which can operate on-line, ie is supplied with a bypass stream, could also be used in principle. The rheological material value functions which can consequently be detected continuously can, at least in principle, be used to conclude changes occurring in the mixture composition. However, it must still be taken into account that changes in polymeric structure parameters which are caused by the compounding process and have retroactive effects directly on the rheological material properties can simulate a change in the mixture composition. This uncertainty in the interpretation of the rheometric results and the insufficient reduction in the non-productive time, still in no way adequate for process control, stand in the way of the use of on-line rheometry for the purpose of determining mixture compositions. Due to the extremely high expenditure on equipment and due to the relatively long non-productive times, on-line FTIR spectroscopy is ruled out of the group of measuring methods with which the composition in terms of proportions by weight of polymer/additive mixtures can be determined really in conformity with process time (=real-time monitoring).

A method of measuring the vapor content of steady and unsteady two-phase flows by means of a gamma-ray density measuring system is known. The gamma radiation is attenuated during passage through the two-phase mixture all the less the greater the vapor content. The remaining residual radiation is registered in a scintillation detector system and converted into an intensity-proportional voltage signal. The medium to be investigated flows through a thin-walled tube. However, the measuring system is not suitable for polymer melts, which are under high pressure at high temperature.

The object was to find a method of continuously detecting and quantifying the composition in terms of proportions by weight of polymer/additive mixtures which are produced in compounding processes. In so doing, it should be possible to determine the relevant formulation data or the corresponding analogous variables in-line, and consequently substantially without non-productive time, with high precision and good reproducibility.

It has been found that the object can be achieved by a method which is based on the principle of radiometric thickness or density measurement and by an apparatus appropriate for performing this method.

The invention consequently relates to a method of detecting in conformity with process time mixing ratios in plastics and rubber compounding, wherein one uses an apparatus comprising a barrel section (1) with an axial channel (4) of rectangular cross section, with sliding surfaces (5) and (6) for a carriage, which can move on both sides of the barrel section (1) transversely to the axis of the barrel section (1) and bears on the one hand holders (8) for a radiation source and on the other hand a scintillation detector system (9), the narrow sides of the channel (4) facing the sliding surfaces (5) and (6) and the wall thickness of the barrel section (1) being reduced in the region of the axis joining radiation source and detector system, to transirradiate the polymer melt flowing through the channel (4) with the measuring beam emanating from the radiation source and to determine from the reduction in the radiation intensity the proportion by volume $k_F$ in accordance with the formula $$k_F = \frac{1}{[\rho_F \cdot F - \rho_P \cdot \mu_P]} \cdot \left[\frac{1}{L} \cdot \ln\left(\frac{I_{St}}{I_{St,G}}\right) - \rho_P \cdot \mu_P\right]$$

in which
- $k_F$ = percentage proportion by volume of the filler, reinforcing material, pigment or blend component,
- $I_{St}$ = measured radiation intensity on the empty channel (4),
- $I_{St,G}$ = measured radiation intensity on the channel (4) filled with melt,
- $\mu_P$ = mass attenuation coefficient of the polymer,
- $\mu_F$ = mass attenuation coefficient of the filler, reinforcing material, pigment or blend component
- L = transirradiated material length,
- $\rho_F$ = density of the filler, reinforcing material, pigment or blend component and
- $\rho_P$ = density of the polymer at the melt temperature T and the pressure p and to calculate from this the percentage proportion by weight b of the filler, reinforcing material, pigment or blend component in accordance with the equations $$k_P = 1 - k_F, a = \frac{k_P \cdot \rho_P}{[k_P(\rho_F - \rho_P) - \rho_F]} \text{ and } b = 1 - a,$$

wherein $k_P$ stand for the percentage proportion by volume of the polymer and a stands for the percentage proportion by weight of the polymer.

The invention also relates to an apparatus, comprising of a barrel section (1) with an axial channel (4) of rectangular cross section, with sliding surfaces (5) and (6) for a carriage, which can move on both sides of the barrel section (1) transversely to the axis of the barrel section (1) and bears on the one hand holders (8) for a radiation source and on the other hand a scintillation detector system (9), the narrow sides of the channel (4) facing the sliding surfaces (5) and (6) and the wall thickness of the barrel section (1) being reduced in the region of the axis joining radiation source and detector system.

In the case of the method according to the invention, a focused measuring beam, emanating from a radiation source, for example a gamma or X-ray source, radiates through the entire mixture stream flowing through a measuring channel and the measuring channel walls, it being absorbed in part and partially scattered upon passing through these layers of material.

The attenuation of the beam depends on the thickness and the density of the layers of material penetrated. The radiation absorption attributable to the wall thicknesses of the die channel can be determined in a so-called empty tube test, in which the unfilled measuring channel is transirradiated. If the measuring channel dimensions, and consequently the mixture layer thickness, is kept constant, the mixture density can be quantified directly by measuring the intensity of the radiation penetrating the filled measuring channel with the aid of a highly stable X-ray measuring chain. For determining the composition in terms of proportions by weight of polymer/additive mixtures, further physical state variables are additionally measured, namely the local melt pressure p at the point of irradiation with the aid of a precision pressure pickup and the representative mixture temperature T by means of a thermocouple dipping into the thermoplastic stream. By including thermal equations of state, which formulate quite generally the dependence of the material density of a medium on pressure and temperature, the material densities of the individual components can be determined at any time in conjunction with the measured values p and T. Such thermal equations of state include substancecharacteristic material parameters, which are determined in the plotting of so-called p,v,T diagrams and are brought into the measuring and evaluating methods according to the invention as prior information.

If the instantaneous density values of the individual mixture components existing at the point of irradiation are known in this way, the proportions by volume of the individual mixture components in the total volume flow can be determined immediately in parallel with the process by including the radiation intensity measured by the X-ray measuring chain and reduced by the penetration of the mixture stream, and taking into account substancedependent and emitter-dependent mass attenuation coefficients as well as the thickness of the transirradiated mixture layer. These proportions by volume are easy to convert into the required proportions by weight of the polymer/additive mixtures.

The reduction in the radiation intensity dI when transirradiating a layer of material is proportional to the currently applying intensity I, the material density $\rho$, the mass attenuation coefficient $\mu$ and the layer thickness dx:

$$dI = -I \cdot \mu \cdot \rho \cdot dx \qquad (1)$$

Integration gives $$I = I^\circ \cdot exp(-\mu \cdot \rho \cdot L) \qquad (2)$$

in which $I^\circ$ stands for the unattenuated initial intensity of the beam and L for the total transirradiated measuring length. The measurable radiation intensity for the flow channel filled with melt is obtained as $$I_{St,P} = I^\circ \cdot exp[-(\mu_{St} \rho_{St} L_{St} + \mu_P \rho_P L_P)] \qquad (3)$$

If the empty flow channel is transirradiated, the following is measured $$I_{St} = I^\circ \cdot exp(-\mu_{St} \rho_{St} L_{St}) \qquad (4)$$

Equations (3) and (4) give $$I_{St,P} + I_{St} exp(-\mu_P \rho_P L_P) \qquad (5)$$

$$\ln\left[\frac{I_{St}}{I_{St,P}}\right] = \mu_P \cdot \rho_F \cdot L_P \qquad (6)$$

This equation states that the radiation intensity $I_{St}$ determined on the empty channel experiences an attenuation which is fixed directly by the mass attenuation coefficient of the polymer $\mu_P$, the polymer density $\rho_P$ and the channel width $L_P$.

The mass attenuation coefficient of the plastic can be determined by measuring $I_{St,P \text{ at } p=1}$ bar and a defined melt temperature and taking $\rho_P$ for the chosen state variables p,T from table compilations.

For the method according to the invention, equation (5) is to be modified as follows:

$$I_{St,G} = I_{Sr} \exp[-(\mu_P \rho_P L_P + \mu_F \rho_F L_F)] \quad (7)$$

The index F in this stands for filler, reinforcing material, pigment or blend component, the index P for polymer, St for steel and G for mixture. The fictitious measuring lengths $L_F$ and $L_P$ must be determined from the volumetric proportions of the mixture. If a is the percentage parts by weight of polymer and b is the percentage parts by weight of filler, a mass and volume balance gives the equation $$a \cdot \frac{\rho_G}{\rho_P} + b \cdot \frac{\rho_G}{\rho_F} = 1 \quad (8)$$

in which the terms on the left side stand for the percentages by volume of polymer and filler:

$$k_P = a \cdot \frac{\rho_G}{\rho_P} \quad (9a)$$

$$k_F = b \cdot \frac{\rho_G}{\rho_F} \quad (9b)$$

The density of the mixture $\rho_G$ is obtained as $$\rho_G = \frac{\rho_P \cdot \rho_F}{\rho_F \cdot a + \rho_F \cdot b} \quad (10)$$

The dependence of the polymer density $\rho_P$ on the pressure p and temperature T can be directly formulated and calculated by means of a thermical condition equation. Taking this thermical condition equation and equation (10) the effective percentage parts by weight (a) of polymer and (b) of filler, reinforcing material, pigment and blend component can be determined by means of the equations $$k_F = \frac{1}{[\rho_F \cdot \mu_F - \rho_P \cdot \mu_P]} \cdot \left[ \frac{1}{L} \cdot \ln\left(\frac{I_{St}}{I_{St,D}}\right) - \rho_P \cdot \mu_P \right],$$

$$k_p = 1 - k_F,$$

$$a = \frac{k_P \cdot \rho_P}{[k_p(\rho_F - \rho_P) \rho_F]} \text{ and}$$

$$b = 1 - a.$$

Figure 2:
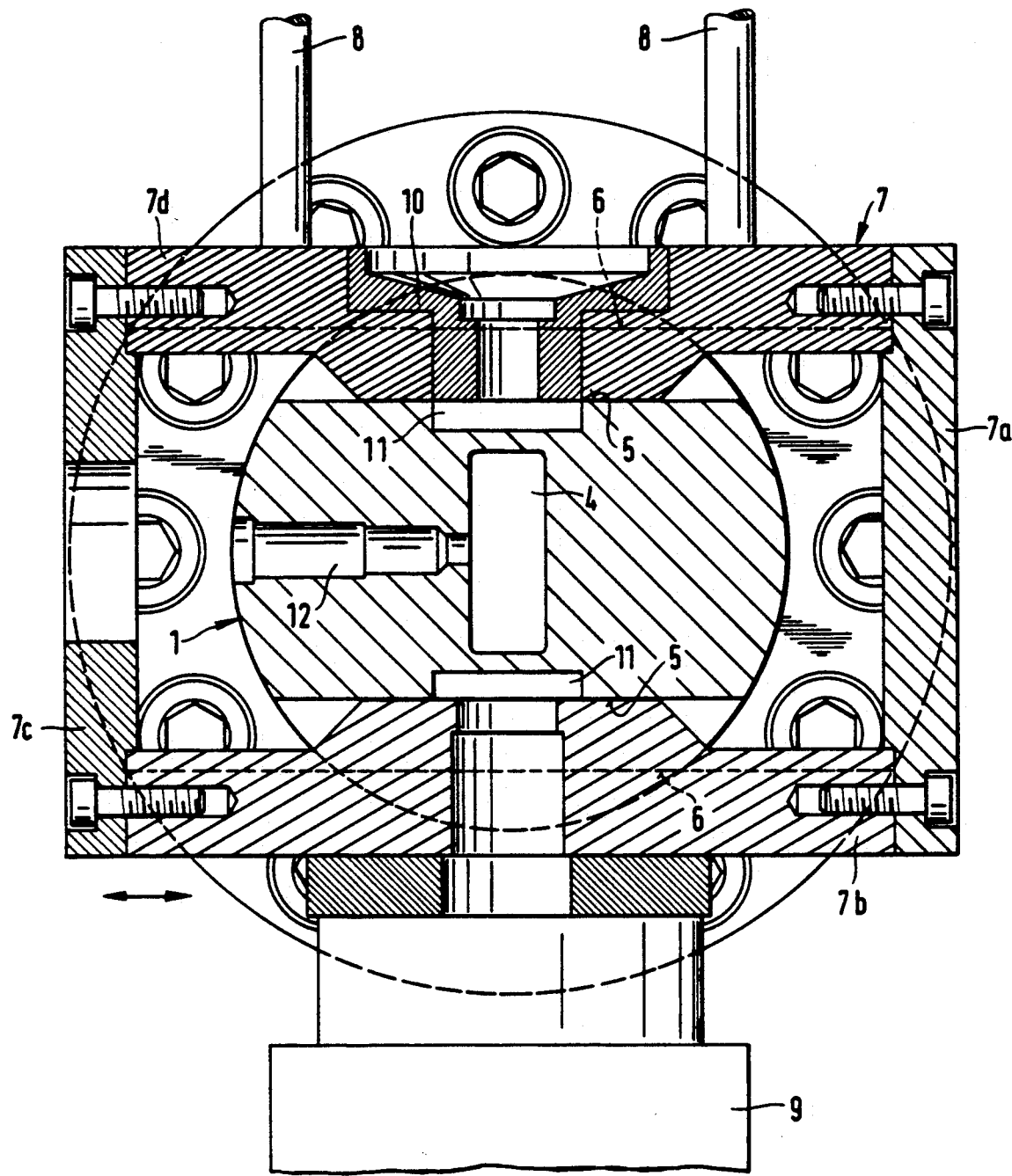

The apparatus according to the invention is represented in FIGS. 1 and 2. FIG. 1 shows a longitudinal section along the principal axis, ie along the direction of extrusion, and FIG. 2 shows a perpendicular cross section A—A in the measurement plane.

According to FIG. 1, the apparatus according to the invention is composed of a barrel section (1), which is fitted between extruder (2) (indicated) and extrusion die (3) (indicated). A channel (4), through which the polymer melt can flow from the extruder (2) to the extrusion die (3), leads axially through the barrel section (1). The barrel section (1) is bevelled on two opposite sides and forms the sliding surfaces (5) and (6) for the carriage (7). This carriage (7) bears on the one hand the holders (8) for the radiation source (not shown) and on the other hand a scintillation detector system (9). For focusing the measuring beam and for axial radiation shielding, a lead shield (10) is attached in the carriage (7) on the side of the radiation source. Furthermore, on both sides of the barrel section (1), the wall thickness is in each case reduced in the measurement plane A—A by recesses (11).

FIG. 2 shows further details. The barrel section (1) is bevelled plane-parallel on two sides and forms the sliding surfaces (5) and (6) (the latter are not visible) for the carriage (7), which is composed of four parts (7a), (7b), (7c) and (7d) for easier disassembly. The channel (4) preferably has a rectangular cross section, the narrow sides of the channel (4) facing the sliding surfaces (5) and (6) of the carriage (7). The longitudinal axis of the cross section is thus identical to the axis between radiation source recesses (11) and scintillation detector (9), which is perpendicular to the axis of the barrel section (1). In the measurement plane there is a bore (12) for a melt pressure pick-up as well as a bore (not shown) for a thermocouple. The dimensions of the channel (4) are chosen such that the transirradiated layer of melt is thicker than 20 mm.

The carriage with the radiation source and the scintillation detector system is movable, preferably vertically, transversely to the axis of the barrel section (1). The movement may be performed manually via a screw spindle, but is preferably carried out by a motor drive, for example by means of a stepping motor.

A displacement pick-up (not shown), connected respectively to the barrel section (1) and the carriage (7), continuously indicates the instantaneous carriage position. In this way, the entire flow channel can be scanned, as a result of which additional information on dwell time spectra, transition functions and velocity fields during the transition from one mixture composition to another are obtained. The above carriage concept only represents one of numerous design variants which are recommendable in particular for laboratory investigations. For production operation, on the other hand, one will rather employ a simplified design, in which the radiation source and detector system are fixed relative to the flow channel (4), ie not displaceably arranged.

In the in-line detecting of the composition in terms of percentages by weight of polymer/additive mixtures, a gamma or X-ray source is recommendable as radiation source for small test chambers with relatively low wall thicknesses and a melt mixture of low density or a bremsstrahlung source (X-ray tube or accelerator) is recommendable as radiation source for measurement volumes of large geometry and/or media of high density. The intensity of the radiation penetrating the flow channel (4) is preferably determined by a highly stable X-ray measuring chain. The measuring chain is composed of a radiation detector and the associated analog electronics. Like the pressure and temperature signals, the intensity measuring signal is digitized and fed to a computer system for measured data detecting, measured data evaluation, dependent variate determination and for data documentation. In the course of the development of process control concepts, in addition a digital controller which is likewise based on these data may be implemented. For the dependent variate determination (=proportions by weight of the individual components), substance-specific parameters (cohesion pressure, cohesion volume, molecular weight of a monomer unit) and mass attenuation coefficients are also required for all individual components and are to be read into the computer in advance.

The method according to the invention and the apparatus according to the invention can be used with advantage for a number of tasks:

Continuous measurement of the density of pure polymers (density constancy)

Plotting of p,v,T diagrams of plastics

Determination of proportions by volume and by weight in polymer/filler or polymer/reinforcing agent mixtures Determination of proportions by weight of pigment in masterbatch preparation Determination of measuring data for statements going further regarding mixing and thermal homogeneity of the material Sensor as basic module for a closed control loop for monitoring and keeping constant proportions of filler.

EXAMPLE

Polypropylene/talc mixtures in different percentage composition were compounded on a co-rotating, closely intermeshing twin screw extruder with variation of the pelletizing die resistance and consequently of the melt pressure p. With the aid of a volumetric premetering of the individual components polypropylene and talc it was endeavored to obtain weight ratios of 80:20, 70:30 and 60:40. The effective talc content of each sample was determined on the one hand off-line by ashing, on the other hand in-line with the aid of the method according to the invention and the apparatus shown in FIGS. 1 and 2. As the table shows, the talc contents determined in such different ways agree very well.

TABLE

| Percentages by weight | |
|---|---|
| measured in-line | determined by ashing |
| 20 | 20.60 |
| 30 | 29.96 |
| 37 | 37.80 |

What is claimed is:

1. A method of detecting in conformity with process time mixing ratios in plastics and rubber compounding, wherein one uses an apparatus comprising a barrel section (1) with an axial channel (4) of rectangular cross section, with sliding surfaces (5) and (6) for a carriage, which can move on both sides of the barrel section (1) transversely to the axis of the barrel section (1) and bears on the one hand holders (8) for a radiation source selected from a group consisting of a gamma source, an X-ray source, and a bremsstrahlungs source, and on the other hand a scintillation detector system (9), the narrow sides of the channel (4) facing the sliding surfaces (5) and (6) and the wall thickness of the barrel section (1) being reduced in the region of the axis joining radiation source and detector system, to transirradiate the polymer melt flowing through the channel (4) with the measuring beam emanating from the radiation source and to determine from the reduction in the radiation intensity the proportion by volume $k_F$ in accordance with the formula $$k_F = \frac{1}{[\rho_F \cdot \mu_F - \rho_P \cdot \mu_P]} \cdot \left[\frac{1}{L} \cdot \ln\left(\frac{I_{St}}{I_{St,G}}\right) - \rho_P \cdot \mu_P\right]$$

in which $k_F$ = percentage proportion by volume of the filler, reinforcing material, pigment or blend component, $I_{St}$ = measured radiation intensity on the empty channel (4), $I_{St,G}$ = measured radiation intensity on the channel (4) filled with melt, $\mu_P$ = mass attenuation coefficient of the polymer, $\mu_F$ = mass attenuation coefficient of the filler, reinforcing material, pigment or blend component L = transirradiated material length, $\rho_F$ = density of the filler, reinforcing material, pigment or blend component and $\rho_P$ = density of the polymer at the melt temperature T and the pressure p and to calculate from this the percentage proportion by weight of b of the filler, reinforcing material, pigment or blend component in accordance with the equations $$k_P = 1 - k_F, \quad a = \frac{k_P \cdot P}{[k_P (\rho_F - \rho_P) - \rho_F]} \text{ and } b = 1 - a,$$

wherein $k_P$ stands for the percentage proportion by volume of the polymer and a stands for the percentage proportion by weight of the polymer.

2. An apparatus, comprising a barrel section (1) with an axial channel (4) of rectangular cross section, with sliding surfaces (5) and (6) for a carriage, which can move on both sides of the barrel section (1) transversely to the axis of the barrel section (1) and bears on the one hand holders (8) for a radiation source selected from a group consisting of a gamma source, an X-ray source, and a bremsstrahlungs source, and on the other hand a scintillation detector system (9), the narrow sides of the channel (4) facing the sliding surfaces (5) and (6) and the wall thickness of the barrel section (1) being reduced in the region of the axis joining radiation source and detector system.

* * * * *

UNITED STATES PATENT AND TRADEMARK OFFICE
CERTIFICATE OF CORRECTION

PATENT NO. : 5,005,194
DATED : April 2, 1991
INVENTOR(S) : HANS-Gerhard Fritz et al It is certified that error appears in the above-identified patent and that said Letters Patent is hereby corrected as shown below:

Column 4, line 60, change "+" to -- = --;

line 64, change "F" to -- p --.

Column 5, line 31, insert the following:

-- $L_P = k_P \cdot L$ (9c)    $L_F = k_P \cdot L$ (9d) --;

and line 36, change "F" to -- p --.

Signed and Sealed this

Twelfth Day of January, 1993

*Attest:*

DOUGLAS B. COMER

*Attesting Officer*    *Acting Commissioner of Patents and Trademarks*